(12) United States Patent
Hirota et al.

(10) Patent No.: US 8,673,854 B2
(45) Date of Patent: Mar. 18, 2014

(54) PROPHYLACTIC AGENT FOR HEART FAILURE

(75) Inventors: Tatsuhiko Hirota, Sagamihara (JP); Kohji Ohki, Sagamihara (JP); Teppei Nakamura, Sagamihara (JP); Toshiaki Takano, Sagamihara (JP)

(73) Assignee: Calpis Co., Ltd., Tokyo (JP)

( * ) Notice: Subject to any disclaimer, the term of this patent is extended or adjusted under 35 U.S.C. 154(b) by 34 days.

(21) Appl. No.: 13/293,993

(22) Filed: Nov. 10, 2011

(65) Prior Publication Data

US 2012/0058947 A1 Mar. 8, 2012

Related U.S. Application Data

(63) Continuation of application No. 12/567,322, filed on Sep. 25, 2009, now abandoned, which is a continuation of application No. PCT/JP2008/055072, filed on Mar. 19, 2008.

(30) Foreign Application Priority Data

Mar. 27, 2007 (JP) ................................ 2007-81638

(51) Int. Cl.
*A61K 38/00* (2006.01)
*A61P 9/00* (2006.01)
*A61K 38/06* (2006.01)
*A61K 38/07* (2006.01)

(52) U.S. Cl.
USPC .......................................... 514/16.4; 514/21.9

(58) Field of Classification Search
None
See application file for complete search history.

(56) References Cited

U.S. PATENT DOCUMENTS

| | | | |
|---|---|---|---|
| 5,449,661 A * | 9/1995 | Nakamura et al. ............ | 514/15.7 |
| 6,534,304 B1 | 3/2003 | Yamamoto et al. | |
| 6,890,529 B1 * | 5/2005 | Mayra-Makinen et al. ........................... | 424/93.45 |
| 2003/0064501 A1 | 4/2003 | Yamamoto et al. | |
| 2006/0205642 A1 * | 9/2006 | Vesely ............................. | 514/12 |
| 2009/0234097 A1 | 9/2009 | Hirota et al. | |
| 2009/0299036 A1 | 12/2009 | Hirota et al. | |
| 2010/0022748 A1 | 1/2010 | Hirota et al. | |

FOREIGN PATENT DOCUMENTS

| | | |
|---|---|---|
| CA | 2616789 A1 | 2/2007 |
| CN | 1784145 A | 6/2006 |
| EP | 1016709 A1 | 7/2000 |
| JP | 2782142 B2 | 5/1998 |
| KR | 10-0404154 B1 | 11/2003 |
| WO | WO 99/16862 A1 | 4/1999 |
| WO | WO 2004/098309 A1 | 11/2004 |
| WO | WO 2006/005757 A2 | 1/2006 |
| WO | WO 2006/041974 A1 | 4/2006 |
| WO | WO 2007/013426 A1 | 2/2007 |
| WO | WO 2007/094342 A1 | 8/2007 |

OTHER PUBLICATIONS

Mizushige et al., "Cases Where ACE Inhibitors Exhibited Effects on Cardiac Hypertrophy," Therapeutics, vol. 30, No. 8, 1996, pp. 945-948.
Office Action for Japanese Application No. 2009-509045, dated Oct. 22, 2012.
Anderson et al.; "Therapeutic Advantage of Converting Enzyme Inhibitors in Arresting Progressive Renal Disease Associated with Systemic Hypertension in the Rat", J. Clin. Invest., vol. 77, Jun. 1986, pp. 1993-2000.
EPO Extended European Search Report, Appl. No. 08722459.8, Feb. 26, 2010.
Hata et al.; "A Placebo-Controlled Study of the Effect of Sour Milk on Blood Pressure in Hypertensive Subjects", Am. J. Clin Nutr., vol. 64, 1996, pp. 767-771.
Hiromichi Suzuki; "ACE Inhibitors and Ca Antagonists as Therapeutic Drugs against Glomerular Diseases", Saishin Igaku, vol. 48, No. 9, (1993) pp. 1404-1409.
JPO International Search Report, Appl. No. PCT/JP2008/055072, Jun. 10, 2008.
Meier, P. et al., "The future of angiotensin II inhibition in cardiovascular medicine," Current Drug Targets—Cardiovascular and Haematological Disorders, vol. 5, No. 1, Jan. 1, 2005, pp. 15-30.
Nakamura et al.; "Antihypertensive Effect of Sour Milk and Peptides Isolated from it That are Inhibitors to Angiotensin I-Converting Enzyme", J. Dairy Sci., vol. 78, No. 6, 1995, pp. 1253-1257.
Nakamura et al.; "Purification and Characterization of Angiotensin I-Converting Enzyme Inhibitors from Sour Milk", J. Dairy Sci., vol. 78, No. 4, 1995, pp. 777-783.
Song et al.; "α- and β-Adrenoceptor Blockade Fail to Prevent High Sodium Diet-Induced Left Ventricular Hypertrophy", Am. J. Hypertens., vol. 10, Aug. 1997, pp. 913-920.
Yamamoto, "Koatsuzai no Ichizuke 6) Angiotensin Henkan Koso (ACE) Sogaizai", Medicine and Drug Journal, 1997, vol. 33, No. 2, pp. 646-650.
Suzuki et al., "Comparison of the Effects of Angiotensin Receptor Antagonist, Angiotensin Converting Enzyme Inhibitor, and their Combination on Regression of Left Ventricular Hypertrophy of Diabetes Type 2 Patients on . . . ," Therapeutic Apheresis and Dialysis, vol. 8, No. 4, 2004, pp. 320-327.
Taiwanese Office Action for Taiwanese Application No. 097110324 dated Mar. 26, 2013.
Chinese Office Action, dated Apr. 11, 2013, for Chinese Application No. 200880009723.0.

(Continued)

*Primary Examiner* — Marcela M Cordero Garcia
(74) *Attorney, Agent, or Firm* — Birch, Stewart, Kolasch & Birch, LLP (57) ABSTRACT

The present invention provides an agent having a suppressive action against the thickening of the heart wall, a prophylactic agent for heart failure containing the above described agent, and functional foods expected to have a prophylactic effect for heart failure. The agent for suppressing heart wall thickening comprises Xaa Pro Pro as an active ingredient.

27 Claims, 2 Drawing Sheets

(56) References Cited

OTHER PUBLICATIONS

Gross et al., "Effect of N-[(S)-1-Carboxy-3-Phenylpropyl]-L-Ala-L-Pro and Its Ethyl Ester (MK-421) on Angiotensin Coverting Enzyme in Vitro and Angiotensin I Pressor Responses in Vivo", Journal of Pharmacology and Experimental Therapeutics, vol. 216, No. 3, 1981, pp. 552-557.

Tribulová et al., "Chronic Disturbances in NO Production Results in Histochemical and Subcellular Alterations of the Rat Heart", Physiological Research, vol. 49, 2000, pp. 77-88.

* cited by examiner

PROPHYLACTIC AGENT FOR HEART FAILURE

This application is a Continuation of U.S. application Ser. No. 12/567,322 filed Sep. 25, 2009, now abandoned which is a Continuation of Application No. PCT/JP2008/055072 filed on Mar. 19, 2008, and for which priority is claimed under 35 U.S.C. §120. This application also claims priority of Application No. 2007-081638 filed in Japan on Mar. 27, 2007 under 35 U.S.C. §119. The entire content of each of the above-identified applications is hereby incorporated by reference.

FIELD OF THE INVENTION

The present invention relates to an active ingredient having a suppressive action on cardiac wall thickening, a prophylactic agent for cardiac hypertrophy and a prophylactic agent for heart failure containing the active ingredient, as well as functional foods containing the active ingredient, the functional foods being expected to have a prophylactic effect against cardiac hypertrophy and heart failure.

Also, the present invention relates to a method for suppressing cardiac wall thickening. Further, the present invention relates to a method for preventing cardiac hypertrophy and heart failure.

BACKGROUND OF THE INVENTION

Recently, the number of those who have a risk factor considered to cause heart diseases, such as smoking, hypertension, hyperglycemia, and hyperlipidemia, have increased in some countries. There is an increasing trend in the number of patients suffering from heart failure. In addition, these pathologic states are not limited to human and the increasing trend in morbidity of such diseases are seen among animals that closely interact with human, such as dogs, cats, other companion animals and pet animals.

Since the pathologic state, classification, and progression of heart failure varies, the disease cannot be readily defined. Yet it can be roughly divided into two types: systolic heart failure and diastolic heart failure. In some cases, these two types simultaneously occur. Systolic heart failure occurs when the heart fails to contract normally. The heart can take in blood but cannot fully pump out adequate blood due to weakened cardiac muscles. As a result, the volume of the blood pumping out to the whole body and lungs decreases and the heart, in particular the left ventricle, can become hypertrophic. On the other hand, diastolic heart failure occurs when the heart wall becomes too stiff to fill up the heart with blood. As a result, blood dams up in the left atrium and lung blood vessels, which could cause congestion. Thus, heart failure generally refers to a condition that heart's pump functions become impaired and hence the heart become incapable of pumping a sufficient amount of blood. Heart failure could cause other changes which further deteriorate functions of the heart, including a decrease in blood volume and congestion of blood in the veins and lungs.

Examples of primary diseases that may cause heart failure include increased pressure overload by hypertension, aortostenosis and the like, cardiac hypertrophy with heart wall thickening by volume overload and the like by valvular disease. Meanwhile, after the onset of myocardial infarction, heart wall thickening may be developed in injury tissues as a spontaneous reaction for functional recovery. Also, agnogenic myocardiopathy of unexplained origins, such as myocardosis, may also cause heart wall hypertrophy. Continuous mechanical load to the heart triggers a gradual decrease in the contractile power of the cardiac muscles, followed by reduction in cardiac performance, and eventually progresses to ventricular arrhythmia, heart ischemia, coronary artery disease, and congestive heart failure.

Considering the situation, a compound having the suppressive action against heart wall thickening is useful for prophylaxis and treatment of cardiac hypertrophy and heart failure.

As a method for improving heart wall thickening, in the case of cardiac hypertrophy caused by hypertension and the like, for instance, treating stem-cause hypertension can improve heart wall thickening in some cases. However, the action is not satisfactory and also some antihypertensive drugs have no effects (*Am J Hypertens.* 1997 August; 10(8): 913~20). Also, even when hypertension is improved, heart wall thickening remains unimproved in many cases. In such cases there is still a risk for the onset of heart failure.

Effective drugs for treating heart failure include angiotensin converting enzyme inhibitors (ACEI), such as Enalapril, which inhibits an enzyme converting angiotensin I to angiotensin II having a hypertensive action (i.e. angiotensin converting enzyme; ACE), and has a hypotensive action. In addition, the antihypertensive drug reportedly improves the progression of renal damage at the same time as lowering blood pressure (*J. Clin. Invest.*, 77, 1993-2000, 1986). Yet on the other hand, for heart failure induced by various primary diseases, the ACE inhibitors are not effective for all cases. Rather there is a risk of developing acute renal failure accompanying lowering blood pressure and therefore it has been pointed out that careful administration is required (*Saishin Igaku*, 48:1404 to 1409, 1993). That is, the antihypertensive drug can be insufficient for the prophylaxis of heart failure but also could rather induce renal failure.

Meanwhile, it has been reported that a peptide originated from food materials, such as casein has the ACE inhibitory activity and such peptides are known to have a hypotensive action. However, whether they have a suppressive action against heart wall thickening or not has not been directly demonstrated (Japanese Patent Publication No. 2782142, *J. Dairy Sci.* 1995, 78:777-78, *J. Dairy Sci.* 1995, 78:1253-1257, *Am. J. Clin. Nutr.* 1996, 64:767-771). Additionally, as described above, since the prophylactic and therapeutic effect for heart failure mediated by ACE inhibition is limited, prophylaxis and treatment of the disease which are not dependent on the ACE inhibition are desired.

SUMMARY OF THE INVENTION

The present invention provides a compound or composition having a suppressive action against heart wall thickening independently of the ACE inhibitory activity.

Further the present invention provides a prophylactic agent for heart failure containing the above described compound or composition.

In addition, the present invention provides functional foods expected to have a prophylactic effect for heart failure containing the above described compound or composition.

Further the present invention provides a method for suppressing heart wall thickening, which method includes administration of the above described compound or composition to a subject.

In addition, the present invention provides a method for preventing heart failure, which method includes administration of the above described compound or composition to a subject.

The present invention is also a use of the above described compound or composition in production of a pharmaceutical for suppressing heart wall thickening. In particular, the present invention is a use of the above described compound or composition in production of a pharmaceutical for preventing cardiac hypertrophy. Yet, the present invention is a use of the above described compound or composition in producing a pharmaceutical for preventing heart failure.

The present inventors have discovered that a tripeptide having a specific structure Xaa Pro Pro (wherein Xaa is any naturally occurring amino acid) has a suppressive action against heart wall thickening, and have reached to invent a pharmaceutical and functional foods useful for prophylaxis of heart failure. Concrete contents of the present invention are as follows:

The present invention provides an agent for suppressing heart wall thickening containing Xaa Pro Pro as an active ingredient.

The present invention also provides a prophylactic agent for cardiac hypertrophy having the above described suppressive action against heart wall thickening.

In addition, the present invention provides a prophylactic agent for heart failure having the above described suppressive action against heart wall thickening.

In addition, the present invention provides functional foods containing a prophylactic agent for heart wall thickening.

The present invention provides a method for suppressing heart wall thickening, which method includes administration of Xaa Pro Pro or a composition containing Xaa Pro Pro to a subject.

In addition, the present invention also provides a method for preventing cardiac hypertrophy, which method includes administration of Xaa Pro Pro or a composition containing Xaa Pro Pro to a subject.

In addition, the present invention provides a method for preventing heart failure, which method includes administration of Xaa Pro Pro or a composition containing Xaa Pro Pro to a subject.

The present invention is also a use of Xaa Pro Pro or a composition containing Xaa Pro Pro in producing a pharmaceutical for suppressing heart wall thickening. In particular, the present invention is also a use of Xaa Pro Pro or a composition containing Xaa Pro Pro in producing a pharmaceutical for preventing cardiac hypertrophy. The present invention is also a use of Xaa Pro Pro or a composition containing Xaa Pro Pro in producing a pharmaceutical for preventing heart failure.

Preferably Xaa Pro Pro is Val Pro Pro and/or Ile Pro Pro.

In other embodiment of the present invention, the active ingredient Xaa Pro Pro is derived from an animal milk casein hydrolysate or a concentrate thereof.

In other further embodiment of the present invention, the active ingredient Xaa Pro Pro is originated from a fermented product obtained by fermenting a raw material containing a milk protein with a bacterium belonging to the species *Lactobacillus helveticus*.

Preferably the bacterium belonging to the species *Lactobacillus helveticus* is *Lactobacillus helveticus* CM4 strain (FERM BP-6060).

DESCRIPTION OF THE PREFERRED EMBODIMENTS

The agent for suppressing heart wall thickening according to the present invention comprises a tripeptide with a specific structure of Xaa Pro Pro as an active ingredient. The term "agent" herein is not restricted to a pharmaceutical but refers to a composition such as a pharmaceutical composition or food composition, or a compound such as a food additive. The term "agent for suppressing heart wall thickening" used in the present invention refers to a compound or composition having an action to suppress progress of lesions of heart wall thickening, an action to improve lesions of heart wall thickening, or a prophylactic effect for the onset of heart wall thickening.

The Xaa in the active ingredient Xaa Pro Pro according to the present invention may be any naturally occurring amino acid. Concrete examples include Val Pro Pro (valine proline proline), Ile Pro Pro (isoleucine proline proline), Ser Pro Pro (serine proline proline), and Leu Pro Pro (leucine proline proline). Preferred are Val Pro Pro and Ile Pro Pro with Val Pro Pro being more preferred. As the active ingredient, the agent may contain a combination of two or more of the tripeptides Xaa Pro Pro, as exemplified by a combination of Val Pro Pro and Ile Pro Pro.

The active ingredient Xaa Pro Pro may be an chemically synthesized tripeptide or naturally occurring tripeptide.

As an chemical synthetic method of tripeptide Xaa Pro Pro, a common method such as solid phase method (Boc method and Fmoc method) and liquid phase method can be employed. For instance, the peptide may be synthesized using an automatic peptide synthesizer such as a peptide synthesizer (PSSM-8type) manufactured by Shimadzu Corporation. With regard to reaction conditions for the peptide synthesis and the like, those skilled in the art can arbitrarily set appropriate reaction conditions and the like, based on their technological common knowledge depending on the synthesis method to be selected and desired tripeptide Xaa Pro Pro.

Alternatively, as the naturally occurring peptide, the tripeptide may be originated from an animal milk casein hydrolysate or a concentrate thereof, as well as may be originated from a fermented product obtained by fermenting a food material containing a protein with fungi or bacteria such as *Aspergillus* and *Lactobacillus*.

In cases where the animal milk casein hydrolysate or the concentrate thereof, or the fermented product obtained by fermenting the raw material containing the milk protein with the bacterium belonging to the species *Lactobacillus helveticus*, besides the tripeptide Xaa Pro Pro which is the active ingredient according to the present invention, free amino acids may be contained. Furthermore, in addition to the above described peptide and free amino acids, for example, lipids, ash, carbohydrates, dietary fibers, water and the like, all of which are normally contained in commercially available animal milk caseins or milk proteins may be contained. Additionally, as required, a part or all of the appropriate components among these may be taken out.

The active ingredient Xaa Pro Pro according to the present invention may be originated from an animal milk casein hydrolysate or a concentrate thereof obtained by a method of hydrolyzing an animal milk casein with a group of enzymes yielding Xaa Pro Pro, in particular Val Pro Pro and Ile Pro Pro and/or a method of fermenting animal milk with *Aspergillus*.

Examples of the animal milk casein include cow milk, horse milk, goat milk, and ewe milk. In particular, cow milk casein being preferably used.

A concentration of casein when the animal milk casein is hydrolyzed or fermented is not restricted but is preferably 1 to 19% by weight in order to efficiently produce the animal milk casein degraded product.

An example of enzyme group is preferably an enzyme group (X) including a peptidase capable of cleaving between Pro and Xaa residues at the carboxyl terminus of the Xaa Pro Pro Xaa sequence.

The enzyme group (X) is preferably a serine type proteinase having serine in the active center or a metal proteinase having a metal in the active center. Examples of the metal proteinase include neutral protease I, neutral protease II and leucyl aminopeptidase. It is preferred that at least one type of these metal proteinases be additionally included in that the desired hydrolysates can be efficiently obtained in a short time, and even in a one-step reaction. Additionally the peptidase capable of cleaving the above described Pro Xaa sequence is preferably an enzyme showing the isoelectric point in the acidic region.

An example of the above described enzyme group or enzyme group (X) is an enzyme group originated from *Aspergillus* such as *Aspergillus oryzae*. Such an enzyme group includes an enzyme group which fungi cells were cultured in an appropriate culture medium and an enzyme produced was extracted with water. Among the enzyme groups originated from *Aspergillus oryzae*, an enzyme group showing the isoelectric point in the acidic region is in particular preferred.

As the enzyme group originated from *Aspergillus oryzae*, commercially available products can be used. Examples thereof are Sumizyme FP, LP or MP (all registered trademark, manufactured by SHINNIHON CHEMICALS Corporation), Umamizyme (registered trademark, manufactured by Amano Enzyme Inc.), Sternzyme B11024, PROHIDROXY AMPL (all trade names, manufactured by Higuchi Shoukai Co., Ltd.), Orientase ONS (registered trademark, manufactured by Hankyu Bioindustry CO., LTD), Denatyme AP (registered trademark, manufactured by Nagase ChemteX Corporation) with Sumizyme FP (registered trademark, SHINNIHON CHEMICALS Corporation) being preferably used.

When these commercially available enzyme groups are used, optimum conditions are usually pre-determined. Yet, conditions such as an amount of enzyme to be used and reaction time can be appropriately altered depending on an enzyme group to be used such that the above described casein hydrolysate can be obtained.

An amount of the enzyme group to be added when the above described animal milk casein is hydrolyzed is, for instance, such that the weight ratio of enzyme group/animal milk casein in a aqueous solution in which the animal milk casein is dissolved is not less than 1/1000, preferably 1/1000 to 1/10, especially preferably 1/100 to 1/10, further preferably 1/40 to 1/10.

The reaction conditions can be appropriately selected depending on an enzyme group to be used such that an intended casein hydrolysate is obtained. A temperature is usually 25 to 60° C., preferably 45 to 55° C. And pH is 3 to 10, preferably 5 to 9, particularly preferably 5 to 8. The enzyme reaction time is usually 2 to 48 hours, preferably 7 to 15 hours.

Termination of the enzyme reaction can be achieved by inactivating the enzyme. Usually the enzyme is inactivated at 60 to 110° C. to stop the reaction.

After the enzyme reaction is terminated, as required, it is preferred to remove precipitates by centrifugation removal and various filter treatments.

Additionally, as required, a peptide having bitterness and/or smell can be removed from the obtained hydrolysate. The removal of such a bitterness component and/or smell component can be done using activated charcoals, hydrophobic resins or the like. For instance, the removal can be carried out by adding the activated charcoals to the obtained hydrolysate in 1 to 20% by weight based on an amount of casein used and by allowing to react the resulting mixture for 1 to 10 hours. Removal of the activated charcoals can be carried out by a known method such as centrifugation and membrane treatment process.

The thus obtained reaction mixture containing the animal milk casein hydrolysate or the concentrate thereof can be added as is to a liquid product such as beverage to be use in the functional foods. In order to improve versatility of the animal milk casein hydrolysate, the above described reaction mixture can be, after concentrated, dried to yield a powdered form.

The content ratio of Xaa Pro Pro contained in the animal milk casein hydrolysate or the concentrate thereof is usually not less than 1% by weight, preferably 1 to 5% by weight based on a total amount of peptides and free amino acids in the animal milk casein hydrolysate or the concentrate thereof. By having the content ratio of not less than 1% by weight, higher actions are expected. Additionally, either when the content ratio of each of Ile Pro Pro or Val Pro Pro contained in the animal milk casein hydrolysate or the concentrate thereof is not less than 0.3% by weight based on a total amount of peptides and free amino acids in the animal milk casein hydrolysate or the concentrate thereof, or when the content ration of a total of Ile Pro Pro and Val Pro Pro is not less than 0.3% by weight, high effects are expected. Further, when 0.3% by weight or more of each of Ile Pro Pro and Val Pro Pro is contained, higher effects are expected.

The active ingredient Xaa Pro Pro according to the present invention may be also originated from a fermented product obtained by fermenting a raw material containing a milk protein with a bacterium belonging to the species *Lactoba-* cillus helveticus. Although the bacterium belonging to the species Lactobacillus helveticus is preferably used individually in the fermentation, other Lactobacillus or the like may be included/contained to the extent that the desired effects according to the present invention is not adversely affected.

As the bacterium belonging to the species Lactobacillus helveticus, a proteinase-producing bacterium capable of highly producing Ile Pro Pro and/or Val Pro Pro is preferred. For instance, a bacterium strain showing a U/OD590 value measured in accordance with a method by Yamamoto et al. (Yamamoto, N. et al. J. Biochem.) (1993) 114, 740), which is based on a method by Twining et al. (Twining, S. Anal. Biochem.) 143 3410 (1984)), of not less than 400 is preferred.

An example of such a preferred bacterium strain is Lactobacillus helveticus CM4 strain (Ministry of International Trade and Industry, National Institute of Bioscience and Human-Technology, 1-1-3 Higashi, Tsukuba, Ibaraki, Japan, Zip code 305, (currently, International Patent Organism Depositary, National Institute of Advanced Industrial Science and Technology, AIST, Tsukuba Central 6, 1-1-1 Higashi, Tsukuba, Ibaraki, Japan, Zip code 305-8566), Accession No.: FERM BP-6060, Date of deposit: Aug. 15, 1997) (hereinafter referred to as CM4 strain). CM4 strain has been registered under the above described accession number under the Budapest Treaty concerning an international approval of microorganism depository on patent procedures, and already patented.

The fermented product obtained by fermenting a raw material containing milk protein with the bacterium belonging to the species Lactobacillus helveticus can be obtained by adding a fermented milk starter containing the bacterium strain belonging to the species Lactobacillus helveticus to a raw material containing the milk protein and by fermenting the mixture on appropriately selected conditions such as fermentation temperature.

A concentrate of the thus obtained fermented product or the like may be powdered with freeze drying, spray drying, or the like and may be used as a powder.

The bacterium belonging to the species Lactobacillus helveticus is preferably used as a starter with sufficiently high activities, which is preliminarily pre-cultured. The number of the bacteria at the beginning is preferably about $10^5$ to $10^9$ cells/ml.

The fermented product obtained by fermenting a raw material containing a milk protein with the bacterium belonging to the species Lactobacillus helveticus, for example, when used for functional foods such as Foods for Specified Health Uses, can be also fermented with yeast in conjunction with the above described bacterium strain belonging to the species Lactobacillus helveticus in order to have better flavor and better palatability. An example of the strain of yeast is preferably the genus Saccharomyces such as Saccharomyces cerevisiae but not restricted thereto. The content ratio of the yeast can be appropriately selected depending on a purpose.

Examples of the raw material containing the milk protein include animal milk such as cow milk, horse milk, ewe milk, goat milk, vegetable milk such as soybean milk, and processed milk of these milk including skimmed milk, reconstituted milk, powdered milk, and condensed milk. Cow milk, soybean milk and processed milk of these milk is preferred and cow milk or processed milk thereof is in particular preferred.

Although the solid content concentration of the milk is not particularly restricted, when the skimmed milk is for instance used, the solid content concentration of non-fat milk is usually about 3 to 15% by weight and preferably 6 to 15% by weight for better productivity.

The above described fermentation is usually carried out by standing or stirring fermentation, for example, by a method of fermenting at a temperature of 25 to 45° C., preferably 30 to 45° C., with a fermentation time of 3 to 72 hours, preferably 12 to 36 hours, wherein the fermentation is terminated when lactic acid acidity reaches 1.5% or more.

The content ratio of Xaa Pro Pro, preferably Ile Pro Pro and/or Val Pro Pro in the fermented product obtained by fermenting the raw material containing the milk protein with the bacterium belonging to the species Lactobacillus helveticus is preferably 10 mg or more, preferably 15 mg or more, in terms of 100 g of a freeze dried product of the fermented product.

As for a dose or intake per day of the agent for suppressing heart wall thickening according to the present invention, in the case of human, usually a dose of about 10 μg to 10 g. preferably 1 mg to 5 g, further preferably 3 mg to 1 g of the active ingredient Xaa Pro Pro, preferably Val Pro Pro and/or Ile Pro Pro may be administrated or taken dividedly in several times in a day.

A period of administration or intake of the agent for suppressing heart wall thickening can be adjusted in many ways in view of age of humans or animals to be administrated or to ingest and/or environments for a risk factor for heart wall thickening of the humans or animals. The period can be for example usually one day or more, preferably 7 days to 365 days.

The prophylactic agent for heart failure according to the present invention comprises the above described tripeptide as an active ingredient.

As for a dose or intake per day of the prophylactic agent for heart failure according to the present invention, in the case of human, usually a dose of about 10 μg to 10 g. preferably 1 mg to 5 g, further preferably 3 mg to 1 g of the active ingredient Xaa Pro Pro, preferably Val Pro Pro and/or Ile Pro Pro may be administrated or taken dividedly in several times in a day.

A period of administration or intake of the prophylactic agent for heart failure can be adjusted in many ways in view of age of human or animals to be administrated or ingest and/or environments for a risk factor against heart failure of the human or animals. The period can be for example usually 1 day or more, preferably 7 days to 365 days.

The prophylactic agent for cardiac hypertrophy according to the present invention contains the above described tripeptide as an active ingredient.

A dose or intake and period of administration or intake of the prophylactic agent for cardiac hypertrophy according to the present invention are same as those of the prophylactic agent for heart failure according to the present invention.

A method of administration or intake of the agent for suppressing heart wall thickening, prophylactic agent for cardiac hypertrophy and prophylactic agent for heart failure according to the present invention is preferably oral administration.

A form of the agent for suppressing heart wall thickening, prophylactic agent for cardiac hypertrophy, prophylactic agent for heart failure according to the present invention, when used as a pharmaceutical, is a form of formulation for oral administration. Examples thereof include tablet, pill, hard capsules, soft capsules, microcapsule, powder, pellet, and solution.

In the case of preparing as a pharmaceutical, for example, pharmaceutically acceptable carrier, adjuvant, vehicle, excipient, antiseptics, stabilizing agent, binder, pH adjusting agent, buffer agent, thickener, gelatinizer, preservatives, antioxidant or the like can be, as required, used. The pharmaceutical can be produced in a unit dose form required pharmaceutical formulation administration generally accepted.

The foods according to the present invention comprises the agent for suppressing heart wall thickening according to the present invention as an active ingredient, and can be, for example, functional foods, such as Foods for Specified Health Uses, which has efficacies such the action for suppressing heart wall thickening, prophylaxis for cardiac hypertrophy, and prophylaxis for heart failure.

An intake to attain such efficacies, for example, in the light of the fact that the functional foods are daily, continuously, or intermittently taken for a long period of time, in the case of human, is usually about 10 μg to 10 g per day, in terms of an amount of the active ingredient Xaa Pro Pro or an amount of Val Pro Pro and/or Ile Pro Pro, preferably 1 mg to 5 g, more preferably 3 mg to 1 g. Depending on the number of intake per day, an intake of the foods such as the functional foods per once can be reduced further to a lower amount than the amount described above.

In cases where the animal milk casein hydrolysate or the concentrate containing the active ingredient Xaa Pro Pro is used as is, in the case of human, the hydrolysate or the concentrate thereof is preferably taken usually in 1 mg to 100 g per day, particularly in about 100 mg to 10 g.

In cases where the freeze dried product of the fermented product containing the active ingredient Xaa Pro Pro is used as is, in the case of human, usually 1 to 100 g per day in terms of a dried amount of the freeze dried product of the fermented product, in particular, about 2 to 50 g is preferably taken.

A period of the intake of the foods according to the present invention, for example the functional foods, is not particularly restricted. The intake for a long period of time is preferred. In order to attain the above described efficacies, for example, the period can be usually not less than one day, preferably 7 days to 365 days.

The foods according to the present invention, for example functional foods, comprise the agent for suppressing heart wall thickening containing the active ingredient Xaa Pro Pro, preferably Val Pro Pro and/or Ile Pro Pro. For instance, the animal milk casein hydrolysate or the concentrate thereof and the fermented product, all of which were obtained in the above described manner, can be added to a variety of foods as they are or in the form of powder or granule. If necessary, a fermented product by *Lactobacillus* other than *Lactobacillus helveticus*, other ingredients used in foods including sugars, proteins, lipids, vitamins, minerals, or flavors, or additives such as various carbohydrates, lipids, vitamins, minerals, sweeteners, flavors, coloring agents, texture improving agents or a mixture thereof may be added to improve nutritional balance, flavor, and/or the like.

The foods according to the present invention, for example the functional foods, can be any form of solids, gels, or liquids. Examples thereof include fermented dairy products such as *lactobacillus* beverages, a variety of processed foods and beverages, dried powders, tablets, capsules, and granule. Further, additional examples can be various beverage, yogurts, fluid diets, jellys, candies, retort-packed foods, tablet candies, cookies, Castella (or Japanese sponge cake), breads, biscuits, and chocolates.

The present invention will now be described in detail by way of examples thereof, but the scope of the present invention is by no means limited by the examples.

EXAMPLES

Example of Peptide Synthesis

The active ingredient according to the present invention Ile Pro Pro and Val Pro Pro were synthesized by the following chemical synthesizing method (Fmoc method). The synthesis was carried out by solid phase method using an automatic peptide synthesizer (PSSM-8type) manufactured by Shimadzu Corporation.

As a solid phase carrier, 50 mg of a resin (SynProPep Resin®, manufactured by Shimadzu Corporation) which is a 2-chlorotrityl(2-Chlorotrityl)type polystyrene resin in which proline protected its amino group with a fluorenylmethyloxy carbonyl group (hereinafter referred to as Fmoc for short) is bound, was used. According to the above described amino acid sequence, Fmoc-Ile, Fmoc-Pro, and Fmoc-Val (100 μmol each) which are protected their amino group with the Fmoc group were reacted in the order of the peptide sequence to obtain a peptide-bound resin in accordance with a conventional method.

This peptide-bound resin was then suspended in 1 ml of a reaction mixture A (10 volume % acetic acid, 10 volume % trifluoroethanol, 80 volume % dichloromethane), allowed to react at room temperature for 30 to 60 minutes. Thereafter the peptides were separated from the resin and the reaction mixture A was filtered with a glass filter. Immediately after the solvent in the filtrate was removed under reduced pressure, 1 ml of reaction mixture B (82.5 volume % trifluoroacetic acid, 3 volume % ethyl methyl sulfide, 5 volume % purified water, 5 volume % thioanisole, 2.5 volume % ethanedithiol, 2 volume % thiophenol) was added and the mixture was allowed to react at room temperature for six hours to uncouple the side chain protecting group. To the resultant 10 ml of anhydrous ether was added to precipitate the peptide, and centrifuged at 3000 revolutions for five minutes to separate. The precipitate was washed with anhydrous ether was several times and then dried by spraying nitrogen gas. The entire volume of the thus obtained unpurified synthetic peptide was dissolved in 2 ml of 0.1N hydrochloric acid aqueous solution and then HPLC using a C18 reverse phase column was carried out in accordance with the conditions below.

Pump: Type L6200 intelligent pump (Hitachi, Ltd); detector: Type L4000UV detector (Hitachi, Ltd) for detection of ultra-violet absorption at 215 nm; column: Micro Bondashere5μC18 (Waters Corp.); eluting solutions: solution A; 0.1% by weight TFA aqueous solution, solution B; acetonitrile with 0.1% by weight TFA aqueous solution; (B/A+B)× 100(%): 0→40% (60 minutes); and flow rate: 1 ml/minute. The eluted fraction showing the maximum absorbance was collected and then freeze-dried to obtain the intended synthetic peptide Ile Pro Pro and Val Pro Pro (5.7 mg and 6.5 mg, respectively). The purified peptide was analyzed using an automatic protein primary structure analyzer (Type PPSQ-10, manufactured by Shimadzu Corporation) from the N-terminal of the peptide. The purified peptide was further analyzed an amino acid analyzer (Type 800 series, manufactured by JASCO corporation) to confirm that the peptide was the one as designed.

Example of Preparation of Animal Milk Casein Hydrolysates

To Casein originated from cow milk (Nippon NZMP Ltd.) (1 g) 99 g of distilled water adjusted to about 80° C. was added and the mixture was stirred well. Subsequently, 1N sodium hydroxide (manufactured by Wako Pure Chemical Industries, Ltd.) solution was added. The mixture was then adjusted to pH 7.0 and a temperature of 20° C. to prepare a substrate solution.

To the obtained substrate solution a commercially available enzyme (registered trademark "Sumizyme FP", manufactured by SHINNIHON CHEMICALS Corporation) was added, which was derived from *Aspergillus oryzae* and contains at least metal protease, serine protease, neutral protease I, neutral protease II and leucyl aminopeptidase such that the enzyme/casein weight ratio of 1/25 was attained. The mixture was allowed to react at 50° C. for 14 hours. Subsequently, the enzymes were inactivated by autoclave at 110° C. for ten minutes, thereby obtaining a casein enzymolytic product solution. Then, the obtained enzymolytic product solution was dried by spray drying to prepare a powder.

Components contained in the obtained powder were analyzed. Proteins were determined by Kjeldahi method and amino acids were measured by an amino acid analyzer. In addition, a difference after subtracting an amount of the amino acids from an amount of the proteins was defined as an amount of peptides. Further, lipids, ash content and water were determined by acid decomposition method, direct ashing method, and drying method by heating under atmospheric pressure, respectively. The remainder after subtracting the amount of each component from 100% was defined as an amount of carbohydrates. The results showed that the powder contained 35.8% by weight amino acids, 45.7% by weight peptides, 6.6% by weight water contents, 0.2% by weight lipids, 4.1% by weight ash contents and 7.6% by weight carbohydrates.

<Measurement of Amino Acids Composing the Peptide>

The powder prepared above was dissolved in an appropriate amount of distilled water and analyzed with an automatic peptide analyzer (trade name PPSQ-10 manufactured by Shimadzu Corporation) to check in what order amino acid is located from the N-terminal in the powder. The automatic peptide analyzer does not detect any free amino acids.

The total amount of the amino acid located at the 5th residue position was 120 pmol and the total amount of the amino acid located at the 6th residue position was 100 pmol. Based on these results, most peptides in the above described powder were found to be dipetptides or tripeptides. Additionally, a proportion of the peptides having Pro as the amino acid at the 2nd residue position markedly increased to 49.5%. A proportion of the peptides having Pro as the amino acid at the 3rd residue position was as high as 29.8%.

Hence the above described powder contains many tripeptides of Xaa Pro Pro.

Thus these peptides were presumably a peptide highly resistant to enzymatic degradation actions of proteases in living bodies.

<Measurement of Peptides Contained in Enzymolytic Products>

For the above described powder of the enzymolytic product, amounts of the tripeptides shown in Table 1 contained in the powder was determined, in accordance with a conventional method, using various chemically synthesized standard peptides. Results are shown in Table 1.

TABLE 1

| Peptide sequence | Amount of tripeptide (µg/ml) in 10 mg/ml of powder |
|---|---|
| Ser Pro Pro | 2.9 |
| Val Pro Pro | 29.5 |
| Ile Pro Pro | 28.1 |
| Phe Pro Pro | 27.2 |
| Other Xaa Pro Pro | 28.8 |

The amount of peptides and free amino acids in a solution in which the above described powder was dissolved and diluted in distilled water was 8.15 mg/ml, and an amount of the peptides was 4.57 mg/ml, an amount of Xaa Pro in the peptides was 514.5 µg. The proportion of Xaa Pro based on a total amount of the peptides and free amino acids in the powder was therefore 6.3% by weight. Further, an amount of Xaa Pro Pro in the peptide was 116.5 µg and it was thus confirmed a proportion of Xaa Pro Pro based on a total amount of the peptides and free amino acids in the powder was 1.4% by weight.

Example of Preparation of CM4 Fermented Milk Animal Feeds

Using fermented milk obtained by fermenting a raw material containing a milk protein with the CM4 strain, animal feeds containing the active ingredient Xaa Pro Pro according to the present invention was prepared.

Commercially available powdered non-fat milk was dissolved in distilled water to the solid content of 9% (w/w) and then autoclaved at 105° C. for ten minutes to sterilize under heating at high temperature. After cooled to room temperature, the resulting solution was inoculated with a CM4 strain starter fermentation solution (the number of the bacteria: $5 \times 10^8$/ml) at 3% (v/w) and left to stand at 37° C. for 24 hours to yield CM4 fermented milk.

The obtained CM4 fermented milk was sterilized at a reaching temperature of 80° C. and then freeze-dried to yield the powder. The obtained freeze dried powder was mixed with commercially available powdered feeds (trade name "CE-2", manufactured by CLEA Japan, Inc.) at the mass ratio of 10:90. The mixture was formed into solid feeds to obtain CM4 fermented milk feeds. The feeds contained 34.1 mg/kg of Val Pro Pro and 17.1 mg/kg of Ile Pro Pro, both of which peptides were originated from the CM4 fermented milk.

[Test1: Effect of Val Pro Pro (VPP) to Suppress Left Ventricle Wall Thickening]

The tripeptide Val Pro Pro (VPP) was tested for the effect of suppressing the thickening of the left ventricle. The test was carried out using three groups of male Wistar rats of seven weeks old (Japan SLC, Inc.), each of which group consisted of 9 to 12 rats. After acclimation for a week, the animals were received: water with a nitrogen monoxide synthesis inhibitor, NG-nitro-L-arginine methylester hydrochloride (L-NAME, manufactured by Sigma) being dissolved at a concentration of 1 g/L; water with L-NAME and VPP being dissolved at a concentration of 1 g/L and 0.3 g/L respectively; or water with L-NAME and angiotensin converting enzyme (ACE) inhibitor, Enalapril at a concentration of 1 g/L and 0.5 mg/L respectively, was supplied ad libitum for eight weeks. The dose of Enalapril was determined such that its activity to inhibit ACE was equivalent to VPP's.

The rats were sacrificed by exsanguination under diethylether anesthesia. The heart was enucleated and then fixed with 10% neutral buffered formalin solution. Annularly-shaped tissue samples were prepared from the fixed heart by horizontally excising the lower part of the atria such that the right ventricle, septum, left ventricle, and coronary artery were included. The specimen were embedded in paraffin and cut into thin sections with a thickness of 3.0 to 3.5 µm using a microtome. Two to five sections per rat were prepared. The sliced thin sections were stained with hematoxylin and eosin and the thickness of the left ventricle wall was measured. As for the measurement of the thickness of the ventricle wall, the thickness of a plural of the points per one section, each of which point was considered to have an average thickness, was actually measured with an ocular micrometer under a microscope. The average thickness was defined as the measured value of the section and subjected to statistical analysis. The measurement and evaluation of the thickness was carried out by a pathologist who was not informed of the name of each sample.

Figure 1:
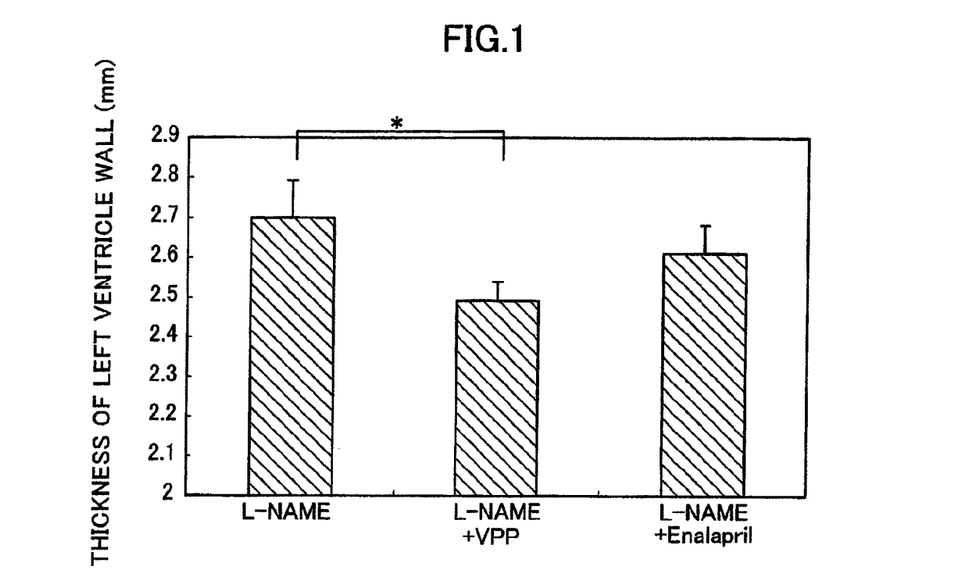
FIG. 1 shows the results of Test 1 examining the effect of Val Pro Pro (VPP) to suppress rat left ventricle wall thickening. The test was conducted using the group of rats administered with L-NAME (11 rats per group), the group of rats administered with L-NAME and Enalapril (9 rats per group), and the group of rats administered with L-NAME and VPP (12 rats per group). The graph represents mean±standard error. Comparisons were demonstrated by the one-sided t-test. The symbol (*) indicates statistical significance ($p<0.05$).

The obtained results are shown in FIG. 1. Compared with the group of rats fed with L-NAME alone, the group of rats fed with L-NAME and VPP showed a decrease in the thickness of the left ventricle wall, indicating that VPP suppressed the thickening of the left ventricle wall and is thus effective in the prophylaxis of heart failure. In addition, since Enalapril of which dose was set so as to have an equivalent ACE inhibitory activity to VPP did not exhibit the effect, it was confirmed that the effect did not depend on the ACE inhibition.

[Test 2: Effect of Val Pro Pro (VPP) to Suppress Right Ventricle Wall Thickening]

Figure 2:
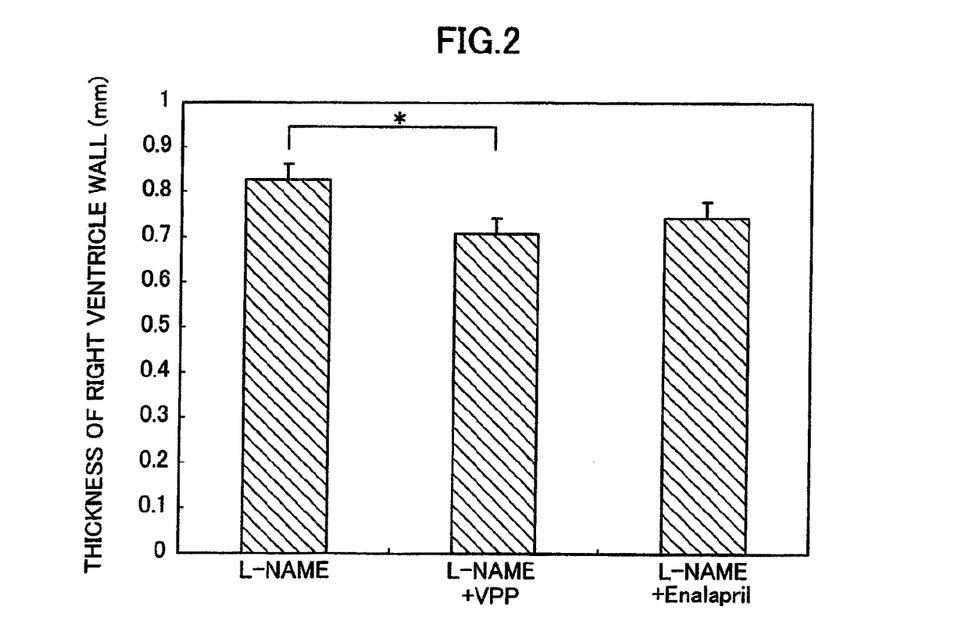
FIG. 2 shows the results of Test 2 examining the effect of Val Pro Pro (VPP) to suppress rat right ventricle wall thickening. The test was conducted using the group of rats administered with L-NAME (11 rats per group), the group of rats administrated with L-NAME and Enalapril (9 rats per group), and the group of rats administered with L-NAME and VPP (12 rats per group). The graph represents mean±standard error. Comparisons were demonstrated by the one-sided t-test. The symbol (*) indicates statistical significance ($p<0.05$).

In order to check the effect of the tripeptide Val Pro Pro (VPP) to suppress the thickening of the right ventricle wall as well, a test was carried out in the same manner as Test 1 and measurement and evaluation were made. The obtained results are shown in FIG. 2. Compared with the group fed with L-NAME alone, the group fed with L-NAME and VPP showed a decrease in the thickness of the right ventricle wall. Hence, VPP also suppressed the thickening of the right ventricle wall and was proven to be effective in the prophylaxis of heart failure. Like in Test 1, Enalapril herein did not show such an effect, it was confirmed that the effect did not depend on the ACE inhibition.

[Test 3: Effect of Ile Pro Pro (IPP) to Suppress Left Ventricle Wall Thickening]

The tripeptide Ile Pro Pro (IPP) was also tested for the suppressive effect against the thickening of the ventricle wall. The test was carried out using three groups of male Wistar rats of seven weeks old (Japan SLC, Inc.), each of which group consist of 9 to 11 rats. After acclimation for a week, the animals received: water with L-NAME (manufactured by Sigma) being dissolved at a concentration of 1 g/L; water with L-NAME and IPP being dissolved at a concentration of 1 g/L and 0.3 g/L respectively; or water with L-NAME and angiotensin converting enzyme (ACE) inhibitor, Enalapril at a concentration of 1 g/L and 0.5 mg/L respectively, ad libitum for eight weeks. The dose of Enalapril was determined such that its activity to inhibit ACE was equivalent to the activity of IPP to inhibit ACE.

The rats were sacrificed by exsanguination under diethyl-ether anesthesia. The heart was enucleated and then fixed with 10% neutral buffered formalin solution. Annularly-shaped tissue samples were prepared from the fixed heart by horizontally excising the lower part of the atria such that the right ventricle, septum, left ventricle, and coronary artery were included. The specimen were embedded in paraffin and cut into thin sections with a thickness of 3.0 to 3.5 µm using a microtome. Two to five sections per rat were prepared. The sliced thin sections were stained with hematoxylin and eosin and the thickness of the left ventricle wall was measured. As for the measurement of the thickness of the ventricle wall, the thickness of a plural of the points for one section, each of which point was considered to have an average thickness, was actually measured with an ocular micrometer under a microscope. The average thickness was defined as the measured value of the section and subjected to statistical analysis. The measurement and evaluation of the thickness was carried out by a pathologist who was not informed of the name of each sample.

Figure 3:
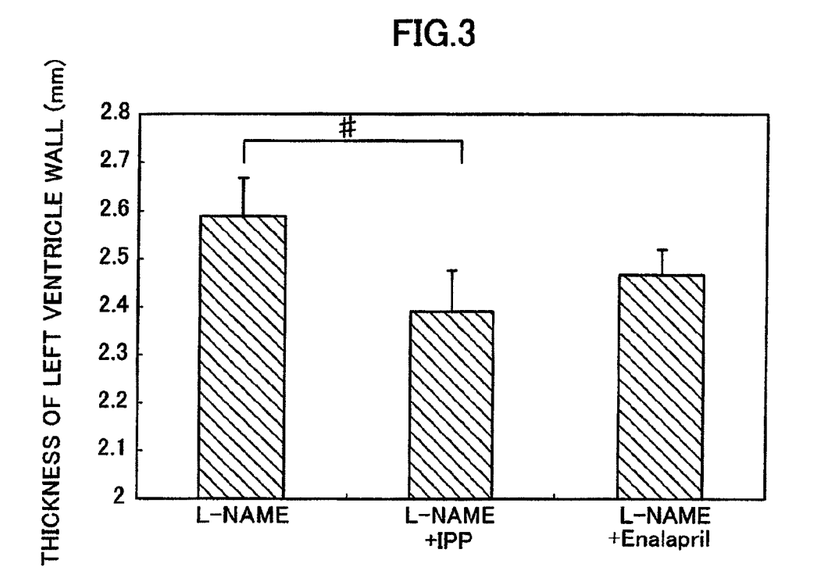
FIG. 3 shows the results of Test 3 examining the effect of Ile Pro Pro (IPP) to suppress rat left ventricle wall thickening. The test was conducted using the group of rats administered with L-NAME (9 rats per group), the group of rats administered with L-NAME and Enalapril (9 rats per group), and the group of rats administered with L-NAME and IPP (11 rats per group). The graph represents mean±standard error. Comparisons were demonstrated by the one-sided t-test. The symbol (#) indicates statistical significance ($p<0.1$).

The obtained results are shown in FIG. 3. Compared with the group of rats fed with L-NAME alone, the group of rats fed with L-NAME and IPP showed a decrease in the thickness of the left ventricle wall, indicating that IPP suppressed the thickening of the left ventricle wall and is thus effective in the prophylaxis of heart failure. In addition, since Enalapril, of which dose was set so as to have an equivalent activity to IPP in terms of ACE inhibition, did not exhibit such an effect, it was confirmed that the effect did not depend on the ACE inhibition.

[Test 4: Effect of Ile Pro Pro (IPP) to Suppress Right Ventricle Wall Thickening]

In order also to check the effect of the tripeptide Ile Pro Pro (IPP) to suppress the thickening of the right ventricle wall, a test was carried out in the same manner as in Test 3, and measurement and evaluation were made.

The test was carried out using three groups of male Wistar rats of seven weeks old (Japan SLC, Inc.), each of which group consist of 9 to 12 rats. After acclimation for a week, the animal received: water with L-NAME (manufactured by Sigma) being dissolved at a concentration of 1 g/L; water with L-NAME and IPP being dissolved at a concentration of 1 g/L and 0.3 g/L respectively; or water with L-NAME and angiotensin converting enzyme (ACE) inhibitor, Enalapril at a concentration of 1 g/L and 0.5 mg/L respectively, ad libitum for eight weeks. The dose of Enalapril was determined such that its activity to inhibit ACE was equivalent to the activity of IPP to inhibit ACE.

The rats were sacrificed by exsanguination under diethyl-ether anesthesia. The heart was enucleated and then fixed with 10% neutral buffered formalin solution. Annularly-shaped tissue samples were prepared from the fixed heart by horizontally excising the lower part of the atria such that the right ventricle, septum, left ventricle, and coronary artery were included. The specimen were embedded in paraffin and cut into thin sections with a thickness of 3.0 to 3.5 µm using a microtome. Two to five sections per rat were prepared. Slices of the thin sections were stained with hematoxylin and eosin and the thickness of the right ventricle wall was measured. As for the measurement of the thickness of the ventricle wall, the thickness of a plural of the points for one section, each of which point was considered to have an average thickness, was actually measured with an ocular micrometer under a microscope. The average thickness was defined as the measured value of the section and the thickness of the ventricle wall of each individual was determined. The measurement and evaluation of the thickness was carried out by a pathologist who was not informed of the name of each sample.

The evaluation of the thickening of the ventricle wall involved the measurement of the thickness of the ventricle wall of six rats of the same age in weeks, which rats were fed with general tap water with no L-NAME being added. The average of those was defined as a reference value. In cases where the thickness of its ventricle wall was larger than the reference value, a rat was defined as one with the thickening, whereas in cases where the thickness of its ventricle wall was equal to or smaller than the reference value, a rat was considered to be normal. Using the number of the rats with the thickening and the normal rats, comparisons by likelihood-ratio test were made. The results were shown in Table 2 below.

TABLE 2

Evaluation results of the thickening of rat right ventricle wall

| Administrated group | Thickening Positive | Normal |
|---|---|---|
| L-NAME | 5 rats | 6 rats |
| L-NAME and IPP (**) | 0 rats | 9 rats |
| L-NAME and Enalapril | 1 rat | 8 rats |

TABLE 2-continued

Evaluation results of the thickening of rat right ventricle wall

| Administrated group | Thickening Positive | Normal |
|---|---|---|

(**): p < 0.01

The obtained results revealed that IPP also suppressed the thickening of the right ventricle wall and thus IPP is also effective on the prophylaxis of heart failure. In addition, since Enalapril, of which dose was set so as to have an equivalent activity to IPP in terms of ACE inhibition, did not exhibit such an effect, it was confirmed that the effect did not depend on the ACE inhibition.

[Test 5: Effect of Ile Pro Pro (IPP) to Suppress Heart Septal Wall Thickening]

In order to check the effect of the tripeptide Ile Pro Pro (IPP) to suppress the thickening of the heart septal wall as well, a test was carried out in the same manner as Test 3 and measurement and evaluation were made.

Figure 4:
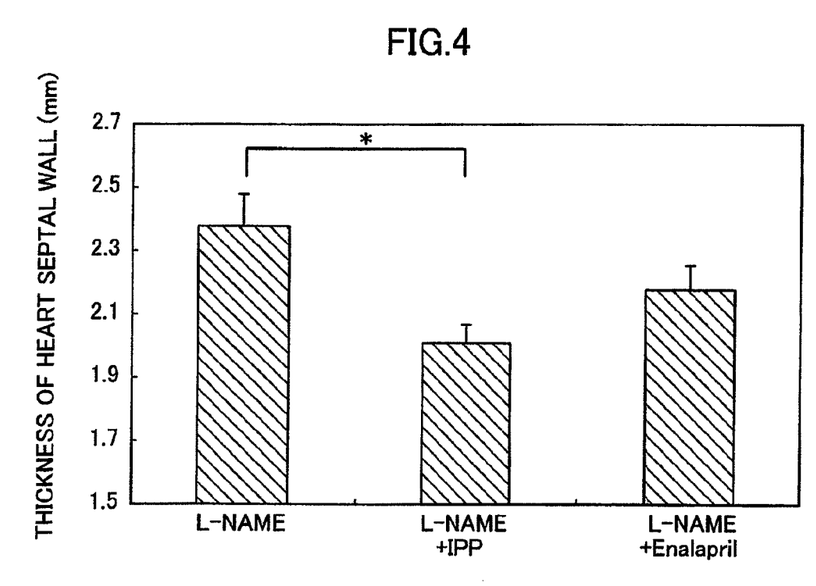
FIG. 4 shows the results of Test 5 examining the effect of Ile Pro Pro (IPP) to suppress rat heart septal wall thickening. The test was conducted using the group of rats administrated with L-NAME (9 rats per group), the group of rats administered with L-NAME and Enalapril (9 rats per group), and the group of rats administered with L-NAME and IPP (11 rats per group). The graph represents mean±standard error. Comparisons were demonstrated by the one-sided t-test. The symbol (*) indicates significant difference ($p<0.05$).

The obtained results are shown in FIG. 4. Compared with the group fed with L-NAME alone, the group fed with L-NAME and IPP showed a decrease in the thickness of the heart septal wall, thus indicating that IPP suppressed the thickening of the heart septal wall and was proven to be effective in the prophylaxis of heart failure. In addition, since Enalapril, of which dose was set so as to have an equivalent ACE inhibitory activity to IPP, did not exhibit the effect, it was confirmed that the effect did not depend on the ACE inhibition.

Since the agent for suppressing heart wall thickening according to the present invention shows effectiveness, even when angiotensin converting enzyme (ACE) inhibitors do not exhibit the suppressive action, the agent is of great use as a pharmaceutical for the prophylaxis and/or treatment of cardiac hypertrophy and heart failure, in particular as a prophylactic agent, which agent is not dependent on the ACE inhibitory activity. In addition, the active ingredient is a naturally occurring tripeptide originated from foods and the like, it is expected that the pharmaceutical with high efficacy and with little concern for side effects is provided. Furthermore, by using or adding the agent for suppressing heart wall thickening according to the present invention in foods or beverages, the functional foods expected to have the prophylactic effect for cardiac hypertrophy and heart failure are provided.

REFERENCE

1. Japanese Patent No. 2782142
2. *Am J Hypertens.* 1997 August; 10(8):913~20
3. *J. Clin. Invest.* 77, 1993-2000, 1986
4. *Saishin Igaku* 48:1404~1409, 1993
5. *J. Dairy Sci.* 1995, 78:777-783
6. *J. Dairy Sci.* 1995, 78:1253-1257
7. *Am. J. Clin. Nutr.* 1996, 64:767-771

What is claimed is:

1. A method for suppressing heart wall thickening, comprising administrating Xaa Pro Pro to a subject in need thereof, wherein the heart wall thickening cannot be suppressed by an ACE inhibitory activity, and wherein said subject has a heart disease risk factor selected from the group consisting of smoking, hyperglycemia and hyperlipidemia.

2. The method for suppressing heart wall thickening according to claim 1, wherein said Xaa Pro Pro is Val Pro Pro and/or Ile Pro Pro.

3. The method for suppressing heart wall thickening according to claim 1, wherein said method comprises a step of obtaining Xaa Pro Pro from an animal milk casein hydrolysate or a concentrate thereof.

4. The method for suppressing heart wall thickening according to claim 3, wherein said method further comprises a step of obtaining the animal milk casein hydrolysate from fermenting an animal milk casein with *Aspergillus*.

5. The method for suppressing heart wall thickening according to claim 3, wherein said method further comprises a step of obtaining the animal milk casein hydrolysate from degrading an animal milk casein with an enzyme derived from *Aspergillus*.

6. The method for suppressing heart wall thickening according to claim 5, wherein said enzyme obtained from said *Aspergillus* is an enzyme obtained from *Aspergillus oryzae*.

7. The method for suppressing heart wall thickening according to claim 1, wherein said method comprises a step of obtaining the Xaa Pro Pro by fermenting a raw material containing a milk protein with a bacterium belonging to the species *Lactobacillus helveticus*.

8. The method for suppressing heart wall thickening according to claim 7, wherein said bacterium belonging to the species *Lactobacillus helveticus* is *Lactobacillus helveticus* CM4 strain (FERM BP-6060).

9. A method of preventing cardiac hypertrophy, comprising administrating Xaa Pro Pro to a subject in need thereof, wherein the cardiac hypertrophy cannot be prevented by an ACE inhibitory activity, and, wherein said subject has a heart disease risk factor selected from the group consisting of smoking, hyperglycemia and hyperlipidemia.

10. The method for preventing cardiac hypertrophy according to claim 9, wherein said Xaa Pro Pro is Val Pro Pro and/or Ile Pro Pro.

11. The method for preventing cardiac hypertrophy according to claim 9, wherein said method comprises a step of obtaining Xaa Pro Pro from an animal milk casein hydrolysate or a concentrate thereof.

12. The method for preventing cardiac hypertrophy according to claim 11, wherein said method further comprises a step of obtaining the animal milk casein hydrolysate from fermenting an animal milk casein with *Aspergillus*.

13. The method for preventing cardiac hypertrophy according to claim 11, wherein said method further comprises a step of obtaining the animal milk casein hydrolysate from degrading an animal milk casein with an enzyme derived from *Aspergillus*.

14. The method for preventing cardiac hypertrophy according to claim 13, wherein said enzyme derived obtained from said *Aspergillus* is an enzyme obtained from *Aspergillus oryzae*.

15. The method for preventing cardiac hypertrophy according to claim 9, wherein said method comprises a step of obtaining the Xaa Pro Pro by fermenting a raw material containing a milk protein with a bacterium belonging to the species *Lactobacillus helveticus*.

16. The method for preventing cardiac hypertrophy according to claim 15, wherein said bacterium belonging to the species *Lactobacillus helveticus* is *Lactobacillus helveticus* CM4 strain (FERM BP-6060).

17. A method for preventing heart failure, comprising administrating Xaa Pro Pro to a subject in need thereof, wherein the heart failure cannot be prevented by an ACE inhibitory activity, and, wherein said subject has a heart disease risk factor selected from the group consisting of smoking, hyperglycemia and hyperlipidemia.

18. The method for preventing heart failure according to claim 17, wherein said Xaa Pro Pro is Val Pro Pro and/or Ile Pro Pro.

19. The method for preventing heart failure according to claim 17, wherein said method comprises a step of obtaining Xaa Pro Pro from an animal milk casein hydrolysate or a concentrate thereof.

20. The method for preventing heart failure according to claim 19, wherein said method further comprises a step of obtaining the animal milk casein hydrolysate from fermenting an animal milk casein with *Aspergillus*.

21. The method for preventing heart failure according to claim 19, wherein said method further comprises a step of obtaining the animal milk casein hydrolysate from degrading an animal milk casein with an enzyme derived from *Aspergillus*.

22. The method for preventing heart failure according to claim 21, wherein said enzyme obtained from said *Aspergillus* is an enzyme obtained from *Aspergillus oryzae*.

23. The method for preventing heart failure according to claim 17, wherein said method comprises a step of obtaining the Xaa Pro Pro by fermenting a raw material containing a milk protein with a bacterium belonging to the species *Lactobacillus helveticus*.

24. The method for preventing heart failure according to claim 23, wherein said bacterium belonging to the species *Lactobacillus helveticus* is *Lactobacillus helveticus* CM4 strain (FERM BP-6060).

25. The method of suppressing heart wall thickening according to claim 1, wherein the subject has heart wall thickening, which cannot be not suppressed by an ACE inhibitory activity.

26. The method for preventing cardiac hypertrophy according to claim 9, wherein the subject has heart wall thickening, which cannot be suppressed by an ACE inhibitory activity.

27. The method for preventing heart failure according to claim 17, wherein the subject has heart wall thickening, which cannot be suppressed by an ACE inhibitory activity.

\* \* \* \* \*

SEQUENCE LISTING

```
<160> NUMBER OF SEQ ID NOS: 1

<210> SEQ ID NO 1
<211> LENGTH: 4
<212> TYPE: PRT
<213> ORGANISM: Artificial
<220> FEATURE:
<223> OTHER INFORMATION: recognition sequence for peptidase
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid

<400> SEQUENCE: 1

Xaa Pro Pro Xaa
1
```